US00PP26946P3

(12) United States Plant Patent
Pavlich

(10) Patent No.: US PP26,946 P3
(45) Date of Patent: Jul. 12, 2016

(54) ×***HEUCHERELLA* PLANT NAMED 'MOJITO'**

(50) Latin Name: ×*Heucherella*
Varietal Denomination: Mojito

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 95 days.

(21) Appl. No.: 14/121,786

(22) Filed: Oct. 17, 2014

(65) Prior Publication Data

US 2016/0113183 P1 Apr. 21, 2016

(51) Int. Cl.
*A01H 5/12* (2006.01)

(52) U.S. Cl.
USPC ..... Plt./441

(58) Field of Classification Search
USPC ..... Plt./441
See application file for complete search history.

(56) References Cited

PUBLICATIONS

New Plants and Flowers Jul. 7, 2014 *Heucherella* with unique, short petioles, retrieved on Mar. 10, 2016, retrieved from the Internet at <http://www.newplantsandflowers.com/heucherella-with-unique-short-petioles/> 2 pp.*

* cited by examiner

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by spring leaves of yellow with a strong red pattern in the center of the leaves, along the veins, summer through winter leaves yellow green with the strong red center, palmately lobed leaves, small white flowers on short flower stalks, medium plant size with multiple crowns, and excellent vigor.

1 Drawing Sheet

Botanical denomination: ×*Heucherella.*
Variety designation: 'Mojito'.

BACKGROUND

The present invention relates to a new and distinct cultivar of ×*Heucherella* and given the cultivar name of 'Mojito'. ×*Heucherella* is in the family Saxifragaceae. ×*Heucherella* 'Mojito' originated from a whole plant mutation of ×*Heucherella* 'Buttered Rum', U.S. Plant Pat. No. 25,040 found in the greenhouse in Canby, Oreg.

Compared to ×*Heucherella* 'Buttered Rum', the new cultivar has yellow to lime as the basic leaf color rather than orange amber to red brown.

Compared to ×*Heucherella* 'Golden Zebra' (U.S. Plant Pat. No. 22,104), the new cultivar has a denser habit with multiple crowns, fewer lobes, and shorter flower spikes.

This new ×*Heucherella* is distinguished by:

1. spring leaves of yellow with a strong red pattern in the center ⅓ of the leaves, along the veins,
2. summer through winter leaves yellow green with the strong red center,
3. palmately lobed leaves,
4. small white flowers on short flower stalks
5. medium plant size with multiple crowns, and
6. excellent vigor.

This new cultivar has been reproduced only by asexual propagation (division and tissue culture using shoot tips). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 9-month-old ×*Heucherella* 'Mojito' in a one gallon container in the greenhouse in spring in Canby, Oreg.

FIG. 2 shows a one-year-old ×*Heucherella* 'Mojito' in the garden in the shade in summer in Canby, Oreg.

DETAILED PLANT DESCRIPTION

The following is a detailed description of the new ×*Heucherella* cultivar based on observations of one and a half-year-old specimens growing in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, fifth edition, 2007.

Plant:

*Form.*—Basal rosette, herbaceous perennial.
*Hardiness.*—USDA Zone 4 to 9.
*Size.*—28 cm tall from top of the foliage to the ground and 48 cm wide.
*Habit.*—Mounding.

*# of crowns*.—About 40.
*Vigor*.—Excellent.
*Roots*.—Fibrous, freely branching, fine, and white in color. Roots develop easily from cuttings.

Leaf:
*Type*.—Simple.
*Arrangement*.—Rosette.
*Shape*.—Ovate.
*Lobing/division*.—5 lobes palmately parted with the terminal the longest and most deeply parted, each with distinctly cut secondary lobes (the depth of the lobes varies with plant maturity and leaf age; leaves become more deeply lobed with maturity).
*Venation*.—Palmate, veins Yellow Green 144A on topside, 148C on bottom side.
*Margins*.—Broadly crenate, older leaves undulate or twist slightly.
*Apex*.—Mucronulate.
*Base*.—Cordate.
*Blade size*.—Grows to 11.5 cm long and 11 cm wide.
*Surface texture*.—Glandular both surfaces.
*Petiole description*.—Grows to 17 cm long and 2 mm wide, glandular hairs, Yellow Green 147C.
*Leaf color*.—Spring, topside, closest to Yellow Green 151B with pattern along veins Greyed Purple 187B, bottom side Yellow Green 151B with the pattern Greyed Purple 183A; summer through winter topside Yellow Green 144A with pattern Greyed Purple 187B, bottom side Yellow Green 146C with pattern Greyed Purple 187B.

Inflorescence:
*Size*.—Grows to 2.3 cm wide and 10 cm long.
*Type*.—Raceme.
*Attitude*.—Upright to semi-upright.
*Density of flowers*.—Medium.
*Number of flowers per raceme*.—About 60.
*Number of raceme*.—20.
*Peduncle*.—Grows to 20 cm tall, 2 mm wide at base, Yellow Green 147C, glandular hairs.
*Pedicel*.—Variable, with glandular hairs, Yellow Green 145B.
*Bloom period*.—May in Canby, Oreg.

Flower bud:
*Size*.—2 mm wide and 3 mm long.
*Description*.—Glandular puberulent, ovoid.
*Color*.—White NN155C.

Flower:
*Type*.—Imperfect.
*Shape*.—Campanulate.
*Size*.—4 mm deep and 5 mm wide.
*Attitude*.—Outward to down-facing.
*Petal description*.—5 in number, lanceolate, 4 mm long and 1 mm wide, some reflexed, tip acuminate, base attenuate, margin entire, glabrous on both sides, White NN155D on both sides.
*Calyx description*.—4 mm deep and 2 mm wide, with 5 lobes, divided ¾ way to the base, campanulate, glandular hairs on outside, glabrous inside, tip obtuse, margin entire, NN155D on both sides.
*Stamen description*.—None.
*Pistil description*.—One central two beaked pistil, 4 mm long and 2 mm wide, White NN155D.
*Fragrance*.—None.
*Lastingness*.—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

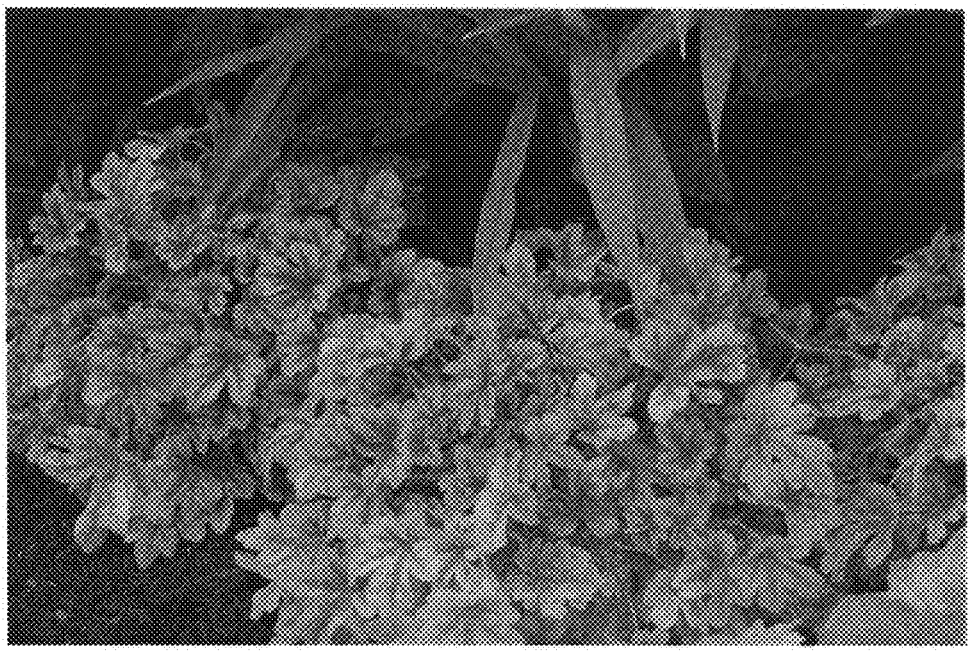

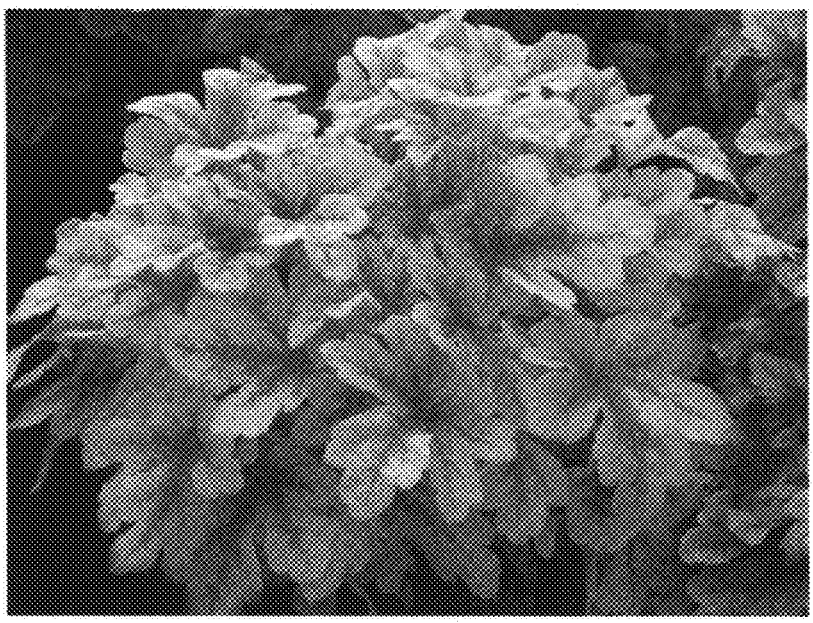
FIG. 1 above, FIG. 2 below